United States Patent [19]

Jones et al.

[11] 4,355,425
[45] Oct. 26, 1982

[54] PANTY WITH A BUILT-IN ELASTIC SYSTEM TO MINIMIZE GATHERING AND PROVIDE A COMFORTABLE, CONFORMING FIT AND METHOD TO ASSEMBLE A PANTY

[75] Inventors: Bradley N. Jones, Cerritos, Calif.; Lawrence H. Sanford, Cincinnati, Ohio

[73] Assignee: The Procter & Gamble Company, Cincinnati, Ohio

[21] Appl. No.: 117,427

[22] Filed: Feb. 1, 1980

[51] Int. Cl.³ .......................... A41B 9/02; A41B 9/04
[52] U.S. Cl. .......................................... 2/402; 2/403; 2/406
[58] Field of Search .................. 2/402, 406, 407, 403, 2/404; 112/121.27

[56] References Cited

U.S. PATENT DOCUMENTS

| | | | |
|---|---|---|---|
| 3,594,820 | 7/1971 | McCurry | 2/406 X |
| 3,613,687 | 10/1971 | Kennedy | 2/406 X |
| 3,856,224 | 12/1974 | Van der Aa et al. | 112/121.27 X |
| 4,031,568 | 6/1977 | Huff | 2/406 |

*Primary Examiner*—H. Hampton Hunter

*Attorney, Agent, or Firm*—John M. Pollaro; Fredrick H. Braun; Richard C. Witte

[57] ABSTRACT

The object of the invention is an improved brief or panty and method of making the same that has porous fabric panels and elastic members that are elastic in all directions. The panty lies flat against the body of the wearer and the fabric panel does not gather adjacent the elastic members.

The panty has an hourglass-shaped panel (10) and an elastic member (11) having hourglass exterior margin (21) and interior margin (22) overlying and bonded to the exterior margin of the fabric panel (10). A functional crotch portion (20) is interposed between the elastic member (11) and the panel (10).

The panty is manufactured by forming an hourglass-shaped panty blank (10) of elastic material having front (19) and rear (18) panel portions; forming an elastic border member (11) from elastic material; superimposing the border member (11) on the hourglass margin of the panty blank (10) and bonding it thereto; and securing corresponding transverse edges of the front (19) and rear (18) panel portions.

8 Claims, 9 Drawing Figures

PANTY WITH A BUILT-IN ELASTIC SYSTEM TO MINIMIZE GATHERING AND PROVIDE A COMFORTABLE, CONFORMING FIT AND METHOD TO ASSEMBLE A PANTY

DESCRIPTION

1. Technical Field

This invention relates to a brief or panty and the construction thereof, and more particularly to a panty or like garment made from elastic nonwoven material and adapted to fit a range of sizes comfortably. The invention also relates to a method of making the panty or brief.

The panty must be constructed of a material that has a fit that both lies flat against the body and is comfortable to wear. The panty must be constructed not to ride up through the crotch or over the buttocks but still provide for a comfortable fit around the leg openings and waist. The panty must be manufactured in a process where elastic portions are provided in or adjacent to the fabric which are inexpensive to attach and manufacture and the complete panty is subject to mass production applications.

2. Background Art

The prior art teaches a panty construction and method of manufacture wherein the elastic members in the panty are attached to the panty fabric while the members are under tension; U.S. Pat. No. 3,613,686 issued to De Woskin on Oct. 19, 1971 and U.S. Pat. No. 4,031,568 issued to Huff on June 28, 1977. Other examples of prior art teach panties having elastic portions secured to the fabric at each panty opening in separate steps: U.S. Pat. No. 4,003,094 issued to Newmar on Jan. 18, 1977; U.S. Pat. No. 3,488,778 issued to Goujon, et al. on Jan. 13, 1970; and U.S. Pat. No. 3,594,820 issued to McCurry on July 27, 1971.

Another group of references show the production of panties through the process of latex dip molding, as seen, for example, in patents issued to Spanel; U.S. Pat. No. 2,119,499 issued on May 31, 1938; U.S. Pat. No. 2,100,572 issued on Nov. 30, 1937; and U.S. Pat. No. 2,158,206 issued on May 16, 1939. Panties of this construction have elastic legbands and waistbands with non-breathable latex material as the panty fabric between the elastic legbands and waistbands.

It is also known in the art to knit panties wherein the elastic is applied to the garment in the form of elastomeric threads selectively incorporated and knit into the fabric where an elastic function is desired. These elastic threads are integrated and knit into the panty fabric at a relatively low tension to minimize gathering. Panty fabric in currently available panties has natural elasticity resulting from the particular knit used. The incorporation of elastic threads in this knit fabric minimizes gathering around elastic portions.

However, none of these patents disclose a panty structure or method of manufacture having the advantages of the current invention.

DISCLOSURE OF THE INVENTION

The garment claimed hereinafter is a panty or brief, made of fabric having a low modulus of elasticity in all directions joined to at least a partial elastic border in superimposed relation and characterized by a lack of gathering at the point where the elastic member is attached to the fabric. In preferred embodiments of the invention, the fabric material has at least 50 percent, or more preferably at least 75 percent elastic extensibility in all directions. Other features desirably embodied in the present invention include: provision of elastic members having the same specific weight modulus of elasticity as the fabric material; use of a single nonwoven elastomeric fabric to produce both the fabric and elastic portions of the panty; provisions for tailoring the extensibility of various regions of the elastic members to provide greater comfort and a better fit for wearers of the panty; and the use of thermoplastic fabric to facilitate further tailoring steps which may be desirable to fit the garment to a particular wearer or class of wearers.

In an especially desired embodiment of the invention, a panty is constructed having a relatively high modulus of elasticity in the vertical dimension and a lower modulus of elasticity in the horizontal dimension when worn.

Also within the scope of this invention are improvements in a stepwise process for producing a panty. A panty blank is formed from elastic fabric having a generally hourglass-shape with a narrow crotch area and front and rear panels. The elastic member or members of the panty are attached to the fabric of a panty blank while the elastic members are in a relaxed condition to form a panty blank assembly. It is desirable that the elastic member be formed in a single piece, which when attached to the fabric of the panty, provides elastic members about each leg opening and each waist portion of the garment, as well as providing reinforced areas which may be joined to form side seams. A preferred method of attaching the elastic member or members to the fabric of a panty blank is to superimpose the elastic members on the panty blank and then to subject the assembly to a hot vacuum-forming process which bonds the elastic member to the fabric of the panty blank while additionally improving the appearance and function of the panty fabric and elastic. The elastic and fabric may be joined by any other conventional means within the scope of the invention as well, provided that the bond joining the elastic and fabric is able to stretch along with the adjacent fabric. The garment is completed by joining the longitudinally opposed flap portions on each side of the panty blank by any of several well known techniques, such as by ultrasonically welding the respective flaps together.

The panty of the current invention is made from a lightweight, nonwoven fabric which is noticeably lighter to wear than existing conventional panties.

The use of nonwoven material and the manufacturing method disclosed herein make the panty of this invention inexpensive. The low cost of the panty of the invention allows the panty to be disposed of after a few launderings.

The panty disclosed herein lies flat against the body and thus is difficult to detect under the outer clothing of the wearer. Conventional panty constructions, wherein a tensioned elastic is applied to a nontensioned fabric, show a gathering of panty fabric which results from a difference in the respective lengths of the unstressed elastic and the fabric to which it is attached. This results in wrinkling of the fabric which is frequently visible through the outer clothing of the wearer, detracting from the wearer's appearance. Such unsightly wrinkling will be present unless the garment is worn with the elastic members stretched until the panty fabric is taut. If the panty is worn with the elastic stretched to its furthest extent allowed by the fabric, the garment would be very uncomfortable. The panty construction disclosed herein requires that the elastic member be applied to an elastic fabric in unstretched condition and as such would not wrinkle the panty fabric on wearing. Due to the construction disclosed herein, there is no wrinkling of the panty fabric adjacent the elastic member and consequently the garment lies flat against the body and does not cause wrinkles which detract from the wearer's appearance. Furthermore, the use of an unstretched elastic element applied to panty fabric allows mass production of panties and eliminates the time-consuming step of stretching the elastic member before attaching it to the fabric.

The panty construction of the current invention incorporates elastomeric fabric and will provide a better fit to wearers of the various physical dimensions within a given size range.

An additional feature of the invention is that use of a relatively wide strip of nonwoven material as the elastic member eliminates discomfort and unsightly bulges which otherwise result from the indentation of a narrow elastic member into the skin of the wearer.

BRIEF DESCRIPTION OF THE DRAWINGS

A preferred embodiment of the disclosed invention can be seen in the following drawings.

While the following disclosure of the preferred embodiments of the invention illustrates the best mode presently known to the inventors to make and use their invention, as well as the best configuration of the invention presently known to the inventors, the inventors do not limit the scope of their invention to the embodiments expressly disclosed, but define the scope of their invention within the scope of the claims following this specification.

DETAILED DESCRIPTION OF THE INVENTION

Figure 1:
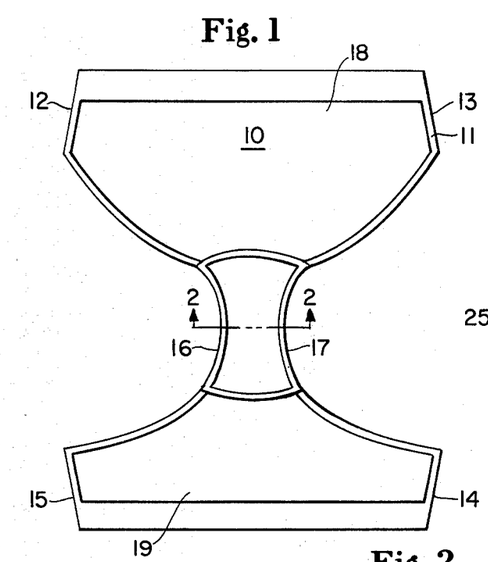
FIG. 1 is a plan view of a panty blank made according to the invention.

The invention may generally be described with reference to FIGS. 1 and 2 which show the overall plan of construction of a panty made according to the present invention. Referring first to FIG. 1, a panty blank 10 is depicted having a substantially hourglass-shaped exterior margin, comprised of panty fabric, having side flaps 12, 13, 14 and 15, crotch portion edges 16 and 17, and front and rear panels 18 and 19. In this particular embodiment of the invention, a functional crotch 20 is attached to the brief in the crotch region thereof as seen in FIG. 3, and in this embodiment, functional crotch 20 overlies panty fabric 10.

A superior fit is obtained when the panty is assembled with material having greater capacity for elongation in the direction substantially perpendicular to the spine. This can be done by assembling the panty from oriented Kraton fabric panels with material having its machine direction parallel to the spine.

A material made of melt-blown Kraton rubber is well suited for the panty fabric material.

The basis weight of this material, about 2.00 ounces per square yard, is lighter than the basis weight of conventional panty material: cotton, 3.12 ounces per yards$^2$ (105.9 g/m$^2$); or nylon, 2.64 ounces/yard$^2$ (89.6 g/m$^2$).

A Kraton G (Kraton G is a trademark of the Shell Chemical Company, One Shell Plaza, P.O. Box 2463, Houston, Tex. 77001) oriented melt-blown nonwoven fabric is particularly suited for this application. Fibers can be melt-blown as taught in U.S. Pat. No. 3,825,380 issued on July 23, 1974 to Harding hereby incorporated by reference. A particularly useful composition contains the following components: Kraton G-1652, 20% by weight stearic acid, 1% by weight TiO$_2$ plus 0.1% by weight antioxidant Irganox 1010 (Irganox is a trademark of Ciba-Geigy, Ardsley, N.Y.). A fabric of this material can be made through a melt-blowing process having a fiber collection surface at an angle of 0°–60° to that of the fiber/air stream. This results in a nonwoven material in which the majority of the fibers are oriented in the direction of travel of the moving air stream of fibers.

The composition of Kraton G rubber and a fatty chemical is mixed in an in-line mixer or in an extruder and put into a conventional extruder for extrusion. The extruder has a melt-blowing head at the nozzle. The Kraton material is extruded through small orifices linearly arrayed in a knife-edge segment. Hot gases pass on either side of the extruded Kraton around the knife edge to carry the material out of the extrusion orifice. The hot gas, such as air or nitrogen, is at a temperature of over 500° F. and moves at high velocity. The hot air takes the extruded rubber and pulls it at a rate faster than extrusion speed out of the orifices. The air stream carries the fibers until they impact the collection plate oriented at 0°–60° with the air stream. The forward end of the fiber contacts the collection plate and is temporarily anchored on the forward end while the latter parts of the fiber are carried along with the air stream over the plate resulting in fibers substantially oriented in the direction of the flowing air stream. This method leaves less fibers perpendicular to the movement of the air stream. Fibers collected on the collection plate form a continuous web of fine fibers that are entangled to form a fabric. Fibers may be connected at their intersection points due to fiber entanglement and from the processing conditions in the melt-blowing process, such as the temperatures of extrusion or of the air stream. By adjusting the plane of the collector surface intersecting the plane of movement of the melt-blown fibers, the fibers collect in an oriented manner due to the velocity of the fiber relative to the collection surface in the combining action of the rapidly moving gas over the collection surface.

A process to make melt-blown Kraton fabrics is disclosed below and shown schematically in FIG. 8. Kraton G-1652, 20% by weight stearic acid, 1% by weight TiO$_2$ and 0.1% by weight Irganox 1010 is mixed in a conventional in-line mixer. The mixed composition is then fed through intake 51 into extruder 50, such as the ⅝" (1.59 cm) screw diameter Wayne Yellowjacket Extruder made by Wayne Machine & Die Co., 100 Furler St., Totowa, N.J. 07512. The extruder 50 has an extrusion screw (not shown) with a 20:1 L/D ratio and a 3:1 compression ratio. The extruder progressively heats the composition to extrusion temperature. In the above disclosed apparatus, the extruder has a first heating zone 53 which heats the mixture to a temperature of 320° F. (160° C.) and a second heating zone 55 which heats the mixture to a temperature of 390° F. (199° C.). The screw turns at 30 RPM resulting in a resin flow through the extruder of approximately 7 grams per minute to extrusion nozzle 57. The extrusion nozzle 57 is heated by conventional means 59, such as heating tapes, up to an extrusion temperature of 390° F. (199° C.). The rubber composition is extruded through an extrusion nozzle 57 having extrusion orifices 61 lying along the edge of a knife-shaped apparatus 63, through an air box 65 having means 67 to allow the inflow of heated air. The air is heated by conventional means not shown, has a temperature of 650° F. (343° C.) and a flow rate of 1150 SCFH (32560 L/min at STP) at 90 PSIG (0.0704 Kg/cm$^2$). The air takes the extruded rubber composition and elongates it as it comes through the extrusion orifices 61 to carry it out the air stream outlet 69 of the extrusion air box 65. The fiber and air stream impact a collection surface 71 angled at 3 inches (7.6 cm) below the air stream outlet 69 a horizontal distance of 4 inches (10.16 cm) from outlet 69. The collection surface 71 is preferably a 60×40 mesh bronze wire screen that is mounted around a vacuum roll 73 having a vacuum of 1.75 inches (4.4 cm) of mercury on vaccum section 74. The collection surface 71 moves around a vacuum mounted roller 73 through a first idler roller 75 and a drive roller 77. Drive roller 77 is driven by conventional means not shown. The fibers collect on the screen to form an oriented melt-blown fabric which is taken off on roll 81.

In this form, Kraton G rubber is an A-B-A block copolymer. The A component is polystyrene and the B component is a copolymer of ethylene and butylene referred to as ethylenebutylene. Kraton G itself cannot be successfully extruded as fibers without melt fracture. The presence of fatty chemicals, such as fatty acid, solubilizes the Kraton G rubber at extrusion temperature to allow it to be extruded into fibers without melt fracture.

At extrusion temperatures, above 100° C., the fatty chemicals solubilize the B block of the Kraton molecule and allow it to be easily extruded by promoting movement of one molecule over another during the extrusion process. At room temperature, the fatty chemicals take a solid form. Thus, the extruded Kraton G fibers then become a rubber material containing solid particles. These solid particles impede the elastic movement of the rubber molecules and have a deliterious effect on the performance of the rubber. The performance of the rubber can be enhanced after extrusion by extracting substantially all the fatty chemicals from the mixture of Kraton and fatty chemicals at room temperature. Fatty chemicals can be successfully extracted from the rubber compound by soaking it in an isopropyl alcohol bath. The alcohol dissolves the fatty chemicals in the fibers and removes them from the rubber mixture resulting in improved rubber qualities. Fatty chemicals are extracted by immersing the Kraton rubber formulation in a solution with a heavy excess of isopropyl alcohol exceeding a 10 to 1 alcohol-rubber ratio.

Melt-blown Kraton fabric of the above stated composition has the properties listed in Table I. Kraton rubbers having 20% stearic acid, Kraton G-1652; 1% TiO$_2$ and 0.1% Irganox 1010 (all compositions listed by weight) have the properties listed in the unextracted column. Kraton rubber fibers having fatty chemicals substantially removed by soaking in isopropyl alcohol are shown in the extracted column. The Kraton fibers measured under the extracted column have less than 1% fatty chemical content.

TABLE I

| | Melt-Blown Fabric | |
|---|---|---|
| | Unextracted | Extracted |
| Basis Weight, oz/yd$^2$ (gm/m$^2$) | 3.29 (111.6) | 2.56 (86.9) |
| Tensile MD, lb/in. (gm/cm) | 5.95 (10.64) | 11.34 (20.27) |
| CD, lb/in. (gm/cm) | 1.45 (2.59) | 3.09 (5.52) |
| Porosity, at 0.5" H$_2$O CFM/ft$^2$ [1.27 cm H$_2$O L/min./cm$^2$] | 220 (6.71) | — |
| Secant Modulus, MD lb/in. (gm/cm) | 1.38 (247) | 1.30 (232) |
| CD lb/in. (gm/cm) | 0.46 (83) | 0.71 (127) |
| Extensibility at failure % of gauge: | 551% | 510% |

Figure 8:
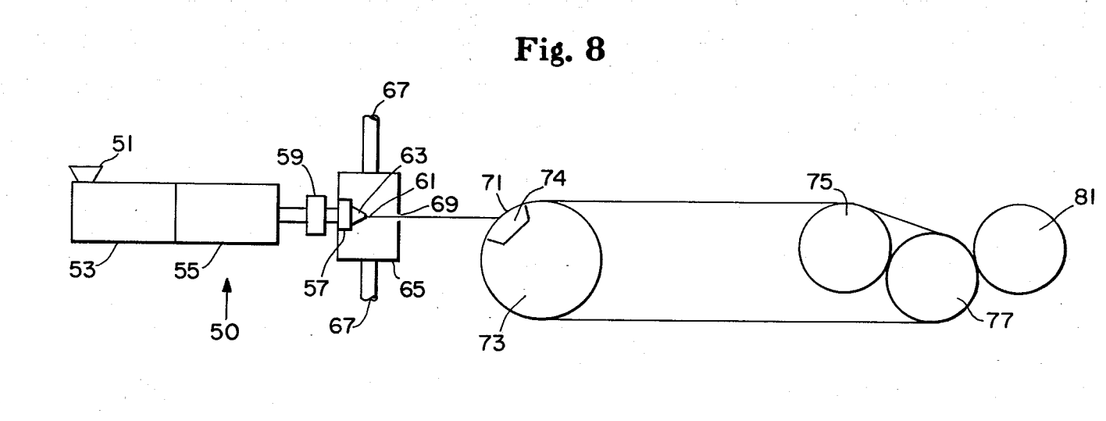
FIG. 8 is a schematic side cross-sectional view of an apparatus to make the melt blown fabric used in the preferred embodiment of the invention.

In Table I, MD refers to machine-direction which is the direction of longitudinal motion of collection surface 71 in FIG. 8. In Table I, CD refers to the cross-machine direction and it is perpendicular to the machine direction.

All tests were performed according to ASTM D1117-77 for Nonwoven Materials. The tensile tests were performed on an Instron testing machine. The tensile tests were performed according to ASTM procedure D-1682 Cut Strip Method. The porosity tests were performed according to procedures outlined in ASTM D-737-75. The secant modulus is the slope of a line drawn on the stress v. elongation curve between points of 0% and 100% elongation.

In one preferred embodiment of the present invention, the material used to form marginal elastic border member 11 may be desirably configured in a "picture frame" shape, as seen in FIG. 3, having a generally hourglass shape, an exterior margin 21 of approximately the same shape and size as the outside margins of panty fabric blank 10 and an interior margin 22 with a shape similar to the exterior margin with a relatively small span between the outer margin 21 and inner margin 22 of the elastic member. While lesser amounts of elastic material will produce a panty having all the necessary elastic, particularly if elastic member portions overlying the side flaps 12, 13, 14 and 15 are deleted, the configuration indicated in the drawing is desirable in order to provide vertical reinforcement of the side of the finished garment. An additional advantage which is realized by using a picture-frame-shaped marginal elastic border member 11 to serve all the elastic and reinforcing functions of the panty is that such an elastic member 11 is easily handled and may be attached to fabric 10 while maintaining all the parts of the elastic member in registration. In the preferred embodiment, the elastic border member 11 is made of the same material as the panty blank fabric 10.

Elastic border member 11 has waist band portions 26 and 27, which will overlie the longitudinal edges of fabric panel 18 and 19 respectively; legband back portions 28 and 29 which are superimposed on the curved portion of panel 18 and overlie the buttocks when worn; and thigh elastic bands 30 and 31 which are to be superimposed on front panel 19 and will overlie the inside of the thighs when worn. Crotch bridges 32 and 33 overlie the longitudinal edges 20c and 20d of the functional crotch element 20 and the crotch elastic members 34 and 35 will overlie the transverse edges 20a and 20b of functional crotch element 20.

In an especially preferred embodiment of the invention, the panty may be made to have areas of different secant moduli of elasticity by varying the width of the elastic member between exterior margin 21 and interior margin 22 at various points. For example, as taught in U.S. Pat. No. 4,031,568 to Huff issued June 28, 1977, hereby incorporated by reference (cited supra on page 1), it is desirable to provide a legband which has a lower modulus of elasticity in the crotch region of the panty than in the outer leg region thereof. Since the leg elastic in the present invention is attached without prestretching it, the use of differential widths of the elastic member to change extensibility of the elastic in selected regions accomplishes the result taught in the '568 reference without requiring a complicated process whereby elastic and panty fabric are joined while tension on the elastic is varied.

To tailor the extensibility of the elastic member, and thus the fit of the panty, an appropriate extensibility is determined for each region of the elastic member and the width of the elastic material is varied to change the cross-sectional area of elastic in order to satisfy the following relation:

$$E = 1/ka$$

where "E" is the desired extensibility, "k" is a constant for a given material which depends on the secant modulus thereof as defined in Table I, and "a" is the area of a cross-section of the material at the point where extensibility is calculated. The extensibility "E" will vary with the cross-sectional area of the nonwoven material and can be adjusted to a desired value by varying the width of a piece of material of given basis weight. The width of the elastic member may vary with the location on the panty, i.e. the waist band portion or leg band portion, and the size of the panty.

A panty that is more comfortable and has a better fit can be made from the construction of this invention by altering the width of the legband back portions 28 and 29. By increasing the width, and therefore the secant modulus of elasticity, of leg band back portions 28 and 29, the panty is more tightly secured to the wearer and is prevented from riding up the buttocks when worn. By decreasing the width, and therefore the secant modulus of elasticity of thigh elastic bands 30 and 31 and crotch elastic members 34 and 35, the panty will stretch more easily around the inner thigh and crotch and be more comfortable to wear.

Figure 4:
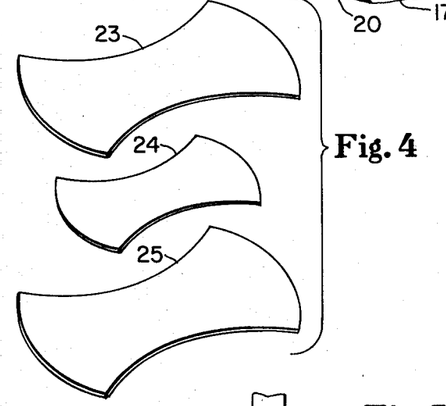
FIG. 4 is an exploded view of the crotch elements of the preferred embodiment of the invention illustrating the manner in which it is assembled.

The first step in assembling the panty is to fabricate the functional crotch element 20. Crotch element 20 has transverse edges 20a and 20b corresponding to the panty blank 10 crotch portion edges 16 and 17, and longitudinal edges 20c and 20d which have the general configuration of crotch bridge 32 and 33. As seen in FIGS. 2 and 4, crotch element 20 is comprised of a skin-contacting porous thermoplastic topsheet 23, an absorbent medium 24 and a moisture-impervious, vapor-pervious backsheet 25. The backsheet 25 structure is more completely described in U.S. Pat. No. 3,989,867, issued to Sisson on Nov. 2, 1976, which incorporated herein by reference. The functional crotch element 20 will absorb and contain small amounts of menstrual fluid or urine.

Topsheet 23 is made from a sheet of polyethylene film having an initial thickness of 0.001 inches ($2.54 \times 10^{-3}$ cm). Topsheet 23 has a structure having capillaries 23a (see FIG. 2a) which can be manufactured, for example, by placing the raw film on the surface of an apertured 1/32 inch (0.079 cm) honeycomb vacuum mold and conformed thereto by applying a vacuum of 8 to 10 inches Hg. (0.296 to 0.345 Kg/sq. cm) to one side of the film and impinging on the other side of the film a stream of air heated to a temperature of 600 degrees Fahrenheit (316° C.) and supplied at a rate of 280 cubic cm per second per square centimeter of material per second. The film forms a structure having a plurality of apertured pores which have sidewalls having an angle of 0°–10°, and preferably 0°, to a line perpendicular to the plane of the topsheet. In this structure, the pores open into the absorbent layer 24.

Backsheet 25 is made from a sheet of polyethylene film having an initial thickness of 0.001 inches ($2.54 \times 10^{-3}$ cm). The backsheet has a structure that is liquid impervious to prevent leakage of any body liquids contained in the absorbent layer, and yet vapor pervious to allow air to circulate in crotch element 20 to make the panties comfortable. This film can be formed on the same honeycomb vacuum-forming machine used to form topsheet 23, except that an 80 mesh molding screen having a wire diameter of 0.005 inches (0.0127 cm), available from Appleton Wire, Industrial Products Division, 714 East Hancock, Appleton, Wis. 54911, is used to form and perforate backsheet 25. The backsheet has a tapered capillary pore structure created by the impression of the film being vacuum-formed around the interstices of the wire mesh. The backsheet 25 has tapered capillary pores 25a (see FIG. 2a) formed by the film being formed into a square shaped pore having walls of curvilinear cross section formed around parallel wires in the molding screen. The tapered capillary pore contains liquid in the absorbent medium through capillary action which prevents liquid from moving through a pore in the direction of increasing cross section and yet allows air to freely circulate through the crotch.

In a preferred embodiment of the invention, topsheet 23 and backsheet 25 of the crotch portion 20 are made of an elastic material. A crotch portion having an elastic topsheet 23 and backsheet 25 will allow the crotch portion 20 to more easily conform to the body and body movements of the wearer and, consequently, be more comfortable. Materials that may be used for topsheet 23 and backsheet 25 are Kraton rubber derivative films (Kraton is a trademark of Shell Chemical Co., One Shell Plaza, Houston, Tex. 77002).

Samples of topsheet 23 made of polyethylene and Kraton films were tested for relevant properties and the results are displayed in Table II below. The Kraton films are of Kraton G-1652, solvent case using Cyclohexane to yield a film 0.001 inches ($2.54 \times 10^{-3}$ cm) thick. The polyethylene used was of a blown film 0.001 inches ($2.54 \times 10^{-3}$ cm) thick and was tested in both the machine direction (MD) [machine direction refers to the direction in which the polyethylene was blown] and cross-machine-direction (CD) [cross machine direction is perpendicular to machine direction]. The topsheet structure tested was vacuum-formed over a 1/32 inch (0.079 cm) honeycomb vacuum mold as disclosed above. The honeycomb structured films were stressed in a Y direction (parallel to a line between two apices of a hexagonal honeycomb) and in an X direction (a direction perpendicular to the Y direction).

TABLE II

|  | Basis Weight oz/yd$^2$ (gm/m$^2$) | Tensile Strength psi (Kg/cm$^2$) | Elongation at Rupture (%) | Set (%) | Stress Relaxation (%) |
|---|---|---|---|---|---|
| X Honeycomb | | | | | |
| MD Polyethylene | 0.67(23) | 597(42.0) | 96 | 40.0 | 31.3 |
| CD Polyethylene | 0.68(23) | 701(49.3) | 80 | — | 30.2 |
| Kraton G-1652 | 1.11(38) | 409(28.8) | 580 | 12.0 | 26.7 |
| Y Honeycomb | | | | | |
| MD Polyethylene | 0.69(23) | 972(68.3) | 89 | — | 32.5 |
| CD Polyethylene | 0.70(24) | 394(27.7) | 28 | — | — |
| Kraton G-1652 | 0.99(34) | 534(37.5) | 648 | 9.0 | 24.4 |

As used herein, Stress Relaxation refers to a testing method having the following steps: a 2" gauge length sample is extended to 100% elongation and relaxed to 0% elongation fives times using a cross head speed of 20 inches/minute on an Instron Model 1122 Testing Machine manufactured by Instron Corporation, 2500 Washington St., Canton, Mass. 02021. On the fifth extension, the sample is held at 100% extension and stress relaxation is measured over time. The measured stress relaxation is:

$$\frac{\text{stress at 100\% extension on 5th cycle} - \text{stress after 30 sec.}}{\text{stress at 100\% extension on the fifth cycle}} \times 100$$

The sample is then measured for Set. The sample is returned to the 0% extension position for 30 seconds. The cross head is then adjusted to pull the sample taut (where tension is first registered) and the length is measured.

$$\% \text{ set} = \frac{\text{taut length} - 2.000" (5.08 \text{ cm})}{2.000" (5.08 \text{ cm})} \times 100$$

Absorbent medium 24 may be any hydrophilic medium capable of absorbing moderate quantities of fluid such as menstrual fluid or urine. A preferred absorbent medium is a Sontara apertured Rayon nonwoven material having a basis weight of 1.7 ox. per square yard (58 gm per square meter), available from E. I. DuPont deNemours, Inc., Texile Fiber Department, Centre Rd., Wilmington, Del. 19898.

It will be understood by those skilled in the art that other apparatus and methods may be used to form the tapered capillary topsheet and backsheet structures described in the Sisson reference and the method cited therein.

Crotch element 20 is assembled by superimposing layers of the respective materials comprising sheets 23, 24, and 25 and die-cutting the assembly. At the same time the crotch assembly is die-cut, it is convenient to cut a plurality of holes about the perimeter of crotch element 20. As explained below, this facilitates the attachment of the crotch to the rest of the garment.

The second step in the manufacture of a panty in accordance with the present invention is to pretreat the panty fabric. The starting material for manfacture of the panty blank 10 is a nonwoven fabric having a basis weight of 2 ounces per square yard (68 gm per square meter) made of melt-blown Kraton G. An Enerpac hydraulic press available from Applied Power Industries, Inc. Enerpac Division, Dept. 10, Butler, Wis. 53007, is fitted with heated platens; a 38×59 mesh semi-twill screen made of 0.008 inch (0.020 cm) filaments on its top pressure platen, and with a 47×56 mesh screen made of 0.009 inch (0.023 cm) filaments and backed by a 0.125 inch (0.318 cm) thick rubber sheet on its bottom platen. The press is heated to 220 degrees Fahrenheit (105° C.), the fabric is placed between the screens of the press, and about 2.34 Kg/cm$^2$ of pressure is applied to the material for 15 seconds. As a result of this treatment, the fabric develops a desirable cloth-like texture which improves the aesthetic appeal of the finished panty garment.

The elements of the garment are assembled and secured to one another in a flat configuration. This may be accomplished by any of a number of joining methods well known in the art, such as by ultrasonic welding, gluing, pressure bonding, heat bonding or the like. One especially preferred method of assembling the garment using apparatus 36 (see FIG. 5) is to mask a 1/32 inch (0.079 cm) hexagonally closepack honeycomb molding surface 38 to define bonding zones which are generally congruent with respect to elastic member 11. The elastic member 11 is then placed on the bonding zone adjacent the molding surface 38 so that elastic member 11 lies over the unmasked portions of the honeycomb molding surface (see FIG. 5). A molding surface 38 having a meshed portion with a honeycomb configuration defined by holes 39 is slidably mounted on surface 37. The crotch 20 is then placed on the molding surface 38 with its perforated perimeter longitudinal edges 20c and 20d overlapping crotch bridges 32 and 33 and crotch transverse edge 20a and 20b overlying crotch elastic members 34 and 35 respectfully. Panty assembly 40 is made by overlying panty blank 10 over elastic member 11 and crotch element 20.

Figure 5:
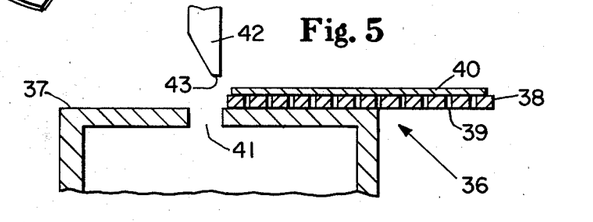
FIG. 5 is a schematic side elevational view of vacuum-forming apparatus used in producing panties in accordance with a preferred embodiment of the invention.

The elements of the panty are joined by passing the molding surface and assembly across a thermal vacuum-forming slot 41 in apparatus 36, as shown in FIG. 5. Apparatus 36 is comprised of a flat surface 37 into which is cut a vacuum slot 41. In this embodiment of apparatus 36, slot 41 is 0.125 inches (0.318 cm) across and 22 inches (56 cm) wide. A vacuum of 10 inches Hg. (0.3453 Kg/cm$^2$) is maintained at this slot. Manifold 42 has an outlet 43 which is 0.25 inches (0.64 cm) across and 22 inches (56 cm) wide. Manifold 42 supplies air at 500 degrees Fahrenheit (260° C.) and 120 cubic feet per minute (56.640 cu.cm/sec) to the opposite side of molding surface 38 and panty assembly 40. Molding surface 38 is passed between a slot 41 and manifold 42 at the rate of 1.4 inches per second (3.6 cm/sec.). As a result of this treatment, the lapped portions of the assembly, which overlie the unmeshed portions of molding surface 38, are conformed to the honeycomb surface of molding surface 38. This perforates the exposed surfaces and at the same time thermally bonds the lapped surfaces together. Crotch portion 20, fabric 10 and elastic member 11 are drawn into engagement through the holes 39 and heat-bonded together, thus binding the three elements of the crotch assembly together.

Figure 2:
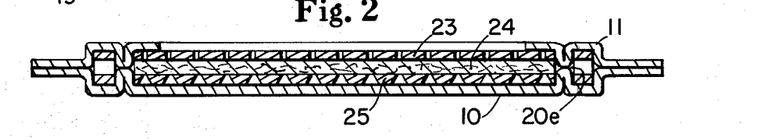
FIG. 2 is a cross-sectional view taken along the line 2—2 of FIG. 1, showing the superimposed relation of the various elements of the panty.
Figure 2A:
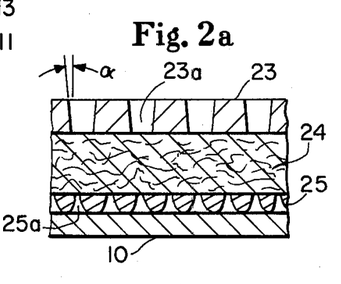
FIG. 2a is an enlarged section of a portion of the crotch element as shown in FIG. 2.
Figure 3:
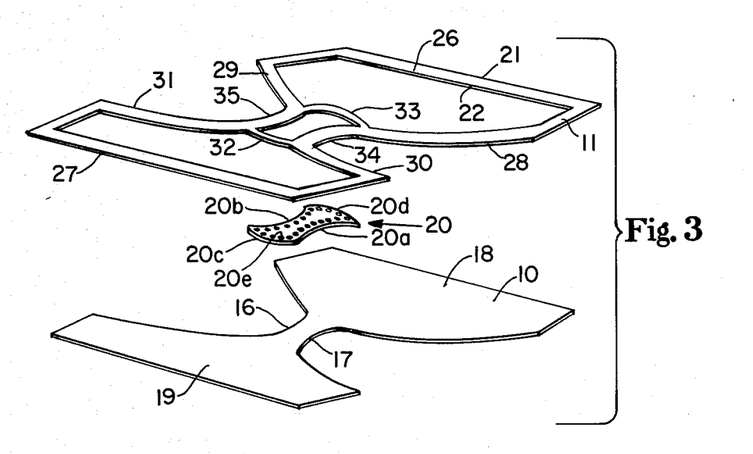
FIG. 3 is an exploded view of the fabric, elastic, and crotch portions of a preferred embodiment of the invention, illustrating the manner in which they are assembled.

As seen in FIG. 2, the final vacuum forming of the panty will draw portions of panty blank 10 and elastic member 11 into holes 20e of crotch 20 and be bonded together to secure the crotch portion in place.

As the panty assembly is vacuum-formed, it is possible to create decorative patterns in selected portions of the garment, especially in portions of elastic member 11, by placing a decoratively perforated metal shield between molding surface 39 and panty assembly 40 and then vacuum-forming the assembly as described above.

The waste material resulting when the panty blank 10 and elastic member 11 are cut from webs of material may conveniently be recovered by any of the methods known to those skilled in the art, such as by disintegrating a nonwoven web into its component fibers or by melting down a thermoplastic web and forming a new web of material therefrom. Such recovery is desirable because a certain amount of material is wasted when a picture-frame-shaped member is cut from a solid sheet of material. It is also possible to reduce this problem by forming webs of material which already have the proper configuration without the need for waste material to be cut away.

While the drawings accompanying this specification depict the manufacture of each panty blank 10 defined separately, it will be appreciated that an integral web comprised of repeating fabric segments joined end to end or side to side may be formed and joined end to end or side to side to a similar web of repeating elastic members, with a crotch element interposed therebetween, before the respective webs are cut in a single step to form elasticized panty blanks in accordance with the present invention. This alternative forming method eases the problems of maintaining registration between the elastic and fabric components of the panty blanks while they are cut and assembled.

The final step in the assembly of a completed panty is to join the transverse edge of panty side flap 12 to the corresponding transverse edge of panty side flap 15, and to join the transverse edge of panty side flap 13 to the corresponding transverse edge of panty side flap 14. This assembly may be joined at the side seams to form a finished panty by any of the numerous conventional techniques, such as gluing, sewing, heat sealing or the like. A perspective view of the panty constructed in the above noted method is seen in FIG. 6.

Figure 7:
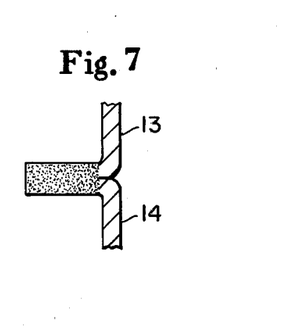
FIG. 7 is a fragmentary view taken along the line 7—7 of FIG. 6, showing a panty side seam.

An especially preferred method to join the side seams and to simultaneously trim the sides of the garment is an ultrasonic welding technique which forms the flanged butt joint shown in FIG. 7, where the flanges extend inwardly from the inside of the completed garment. The seam is sealed using an Ultrasonic Welder with a 0.5 inch (1.27 cm) by 7 inch (18 cm) horn attachment, available from Branson Sonic Power Company, Eagle Rd., Danbury, Conn. 06810. The welder is set at an air pressure of 60 p.s.i.g. (4.22 Kg/cm$^2$), a weld time of 0.5 second and a hold time of 1.0 seconds.

The panty assembly is first folded in half so that the inner surface of the panty is presented outwardly and transverse edges 13 and 14 are adjacent one another. The transverse edge of the folded panty is then inserted between the horn and the anvil of the welder, and the welder is actuated to seal the edges of the panty blank while trimming surplus material from the transverse edges 13 and 14. Transverse edges 12 and 15 are similarly joined to form the second side seal. The panty is then inverted so that the exterior surface of the panty is presented outwardly in the finished garment.

Figure 6:
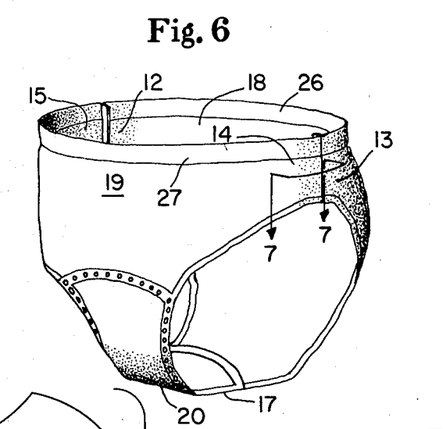
FIG. 6 is a side perspective view of the completed panty.

As seen in FIG. 6, waist portions 18 and 19 are joined in the assembled panty to form a single waist encircling elastic member. The waistband is made of a composite of the fabric of panty back panel 18 and front panel 19 and elastic member waistband portions 26 and 27 respectively. The crotch margin portions 16 and 17 are each looped to form a thigh-encircling portion, and the side flaps 12 and 13 are joined to side flaps 15 and 14 respectively to form vertically reinforced sides in the finished garment.

The foregoing and other advantages will be apparent to those skilled in the art of manufacturing panties and panties themselves. The invention disclosed above has industrial application in producing a panty that is comfortable when worn by a woman or child. The method disclosed teaches a method of high speed manufacture of the panty. During the menstrual period, a moisture impervious backsheet incorporated in the panty prevents leakage of the urine or menses to the outer garments. The backsheet is vapor pervious to make this panty particularly comfortable by allowing air flow through the crotch element.

What is claimed is:

1. A nongathered panty comprising a porous fabric panel means and elastic member means defining waist and leg openings wherein said fabric panel means and said elastic member means are manufactured from a nonwoven material which is elastic in all directions said fabric panel means and said elastic member means being manufactured from a nonwoven material and having the same composition.

2. The panty as claimed in claim 1 wherein said panty fabric panel means and said elastic member means have a basis weight of about 87 gm per square meter, a secant modulus of elasticity of at least 127 gm/cm and an elastic range of extensibility of at least 50 percent.

3. The panty as claimed in claim 1 wherein said fabric panel means comprises a single, generally hourglass-shaped panel defining a narrow crotch portion and front and rear portions having transverse edges; said elastic member means have a generally hourglass-shaped exterior margin overlying the outside margin of the fabric panel means and an interior margin defining the cross sectional area of the elastic member means; said elastic member means is secured to said fabric panel means along the outside margin of said fabric panel means; and said panty is formed by bonding the transverse edges of the rear portion to the transverse edges of the front portions.

4. The panty as claimed in claim 3 wherein there is a functional crotch member interposed between said elastic member means and said fabric panel means upon said narrow crotch portion of said fabric panel means.

5. The panty as claimed in claim 4 wherein there is a functional crotch means overlying said narrow crotch portion of said panel comprising at least three members superimposed upon one another; said members include a porous liquid permeable topsheet member, a moisture impervious, vapor pervious backsheet member, and an absorbent member interposed between said topsheet member and said backsheet member.

6. The panty of claim 1 wherein said elastic member means comprises an elongate elastic member adapted to be attached to a substrate to form an elastic assembly where the elastic assembly is a composite of said elastic member and a fabric panel having at least one site of increased secant modulus of elasticity comprising an elongate portion of elastomeric sheet material which is wider at said at least one site than at other sites along said elongate elastic member.

7. The panty of claim 6, wherein said elastic member means has a region of reduced cross sectional area adjacent the crotch which is more easily extensible than other regions of said elastic member means, resulting in said elastic assembly having a decreased secant modulus of elasticity.

8. The panty as claimed in claim 2 wherein said fabric panel means has a greater modulus of elasticity in the vertical direction, as worn, than in the horizontal direction.

* * * * *